US005616119A

United States Patent [19]
Davis

[11] Patent Number: 5,616,119
[45] Date of Patent: *Apr. 1, 1997

[54] MEDICATED POLYMERIC APPARATUS

[75] Inventor: William M. Davis, Tucson, Ariz.

[73] Assignee: Lathrotec, Inc., Tucson, Ariz.

[ * ] Notice: The term of this patent shall not extend beyond the expiration date of Pat. No. 5,562,652.

[21] Appl. No.: 458,121

[22] Filed: Jun. 2, 1995

Related U.S. Application Data

[63] Continuation-in-part of Ser. No. 319,971, Oct. 7, 1994, Pat. No. 5,562,652.

[51] Int. Cl.⁶ ........................................................ A61N 1/30
[52] U.S. Cl. ............................ 604/19; 604/96; 604/264; 602/48
[58] Field of Search ........................ 604/19, 11, 96, 604/53, 97, 98, 99, 100, 101, 102, 103, 264; 602/48

[56] References Cited

U.S. PATENT DOCUMENTS

| | | |
|---|---|---|
| 2,800,905 | 7/1957 | Simmons et al. .................. 604/349 |
| 3,894,540 | 7/1975 | Bonner, Jr. . |
| 4,343,788 | 8/1982 | Mustacich et al. . |
| 4,479,795 | 10/1984 | Mustacich et al. . |
| 4,529,398 | 7/1985 | Wong et al. . |
| 4,620,527 | 11/1986 | Adams, Jr. . |
| 4,685,455 | 8/1987 | Vrouenraets . |
| 5,098,379 | 3/1992 | Conway et al. . |
| 5,137,671 | 8/1992 | Conway et al. . |
| 5,176,665 | 1/1993 | Watanabe et al. . |
| 5,176,666 | 1/1993 | Conway et al. . |
| 5,185,007 | 2/1993 | Middaugh et al. . |
| 5,236,422 | 8/1993 | Eplett, Jr. . |
| 5,261,896 | 11/1993 | Conway et al. . |
| 5,269,755 | 12/1993 | Bodicky . |
| 5,269,770 | 12/1993 | Conway et al. . |
| 5,334,175 | 8/1994 | Conway et al. . |

Primary Examiner—Corrine M. McDermott
Assistant Examiner—N. Kent Gring
Attorney, Agent, or Firm—Austin R. Miller

[57] ABSTRACT

Water-activated medicated apparatus including a base member at least partially formed from a water vapor permeable material and a water-activated or continuously released medicinal agent located within at least a portion of the base member, wherein the base member permits permeation of water vapor toward and into contact with the water-activated medicinal agent and diffusion of medicinal compound formed from the water-activated medicinal agent outwardly from said base member.

20 Claims, 4 Drawing Sheets

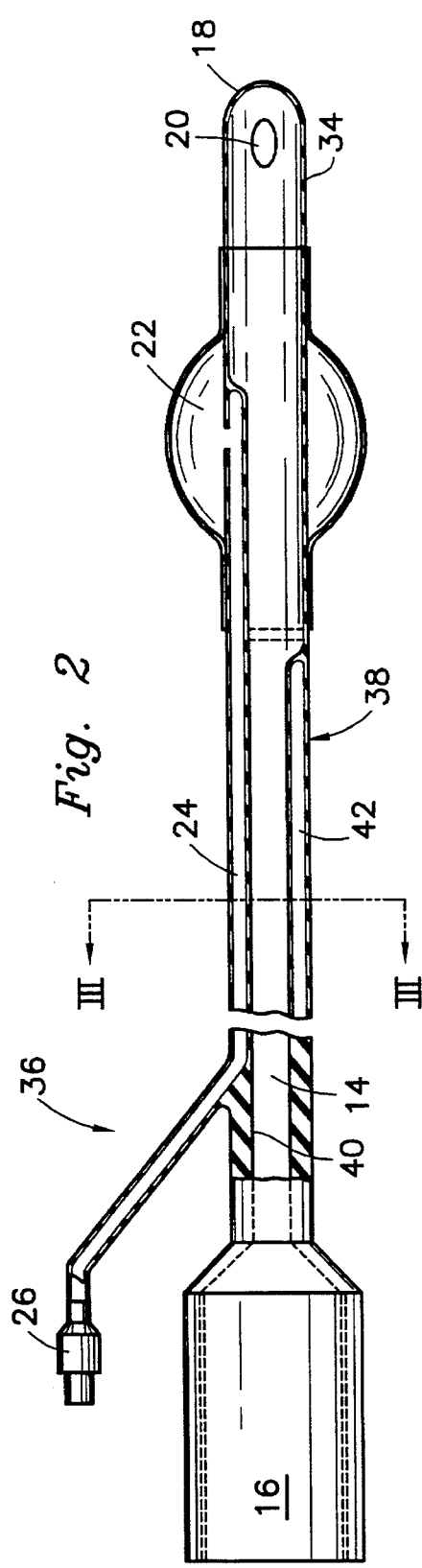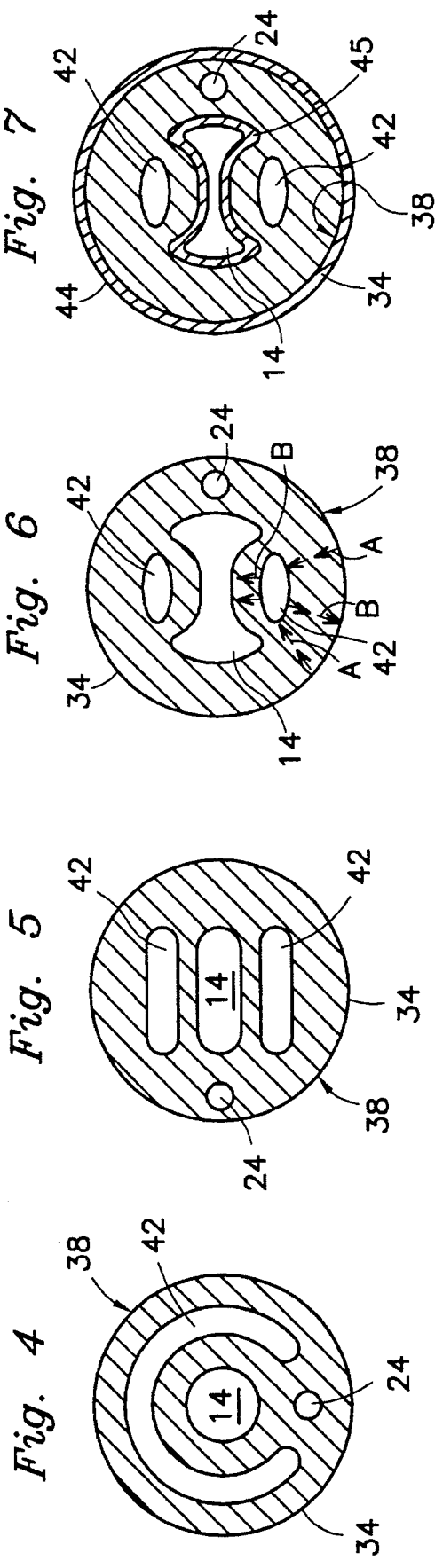

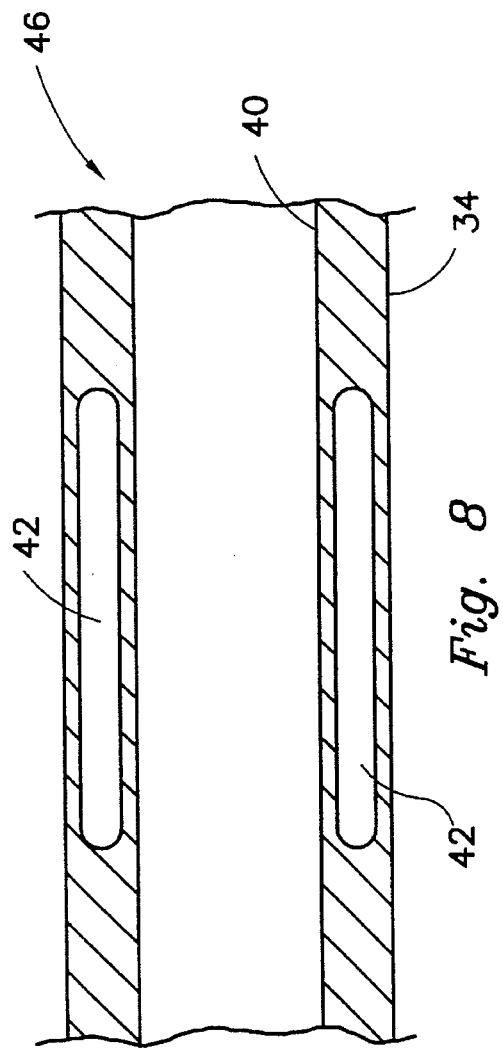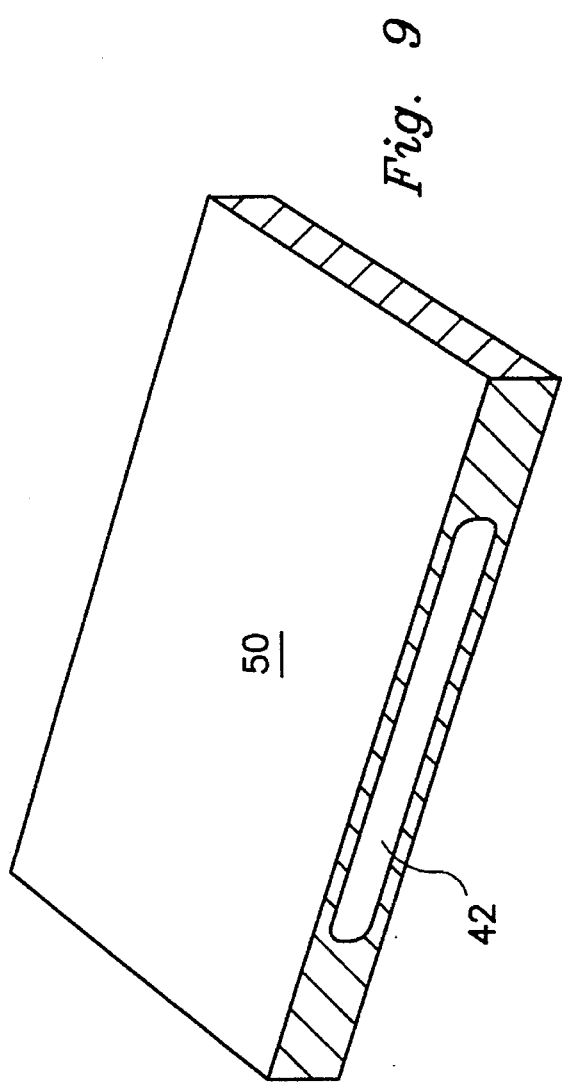

MEDICATED POLYMERIC APPARATUS

This application is a continuation-in-part of application Ser. No. 08/319,971, filed Oct. 7, 1994 U.S. Pat. No. 5,562,652.

FIELD OF THE INVENTION

The present invention relates to medicated devices, particularly to catheters capable of extended indwelling duration having excellent medicament delivery capabilities.

BACKGROUND OF THE INVENTION

In the practice of human and veterinary medicine, it is often desirable and necessary to use various polymeric devices such as urinary catheters, cerebro peritoneal shunts, breast implants, artificial joints, hemodialysis devices and the like to treat or diagnose disease. Such devices, although manufactured from inert polymers, most commonly silicones, are often conduits for infection from surface bacteria or become nonfunctional due to surface blood clotting if they are in prolonged contact with the vascular system. Further, some devices, such as irrigating or drainage tubes and catheters, are uniquely positioned to be therapeutic drug delivery systems. Other devices can be anatomically positioned to effect physiologic function, such as inhibitors or enhancers of fertility and for cancer chemotherapy. All such diagnostic, preventive and/or therapeutic functions of the polymeric devices are dependent upon the unique relation between the polymer and the medicinal agent which will be outlined in this invention.

These devices are often contaminated by bacteria, fungus, viruses and other organisms or infective proteins, resulting in systemic and/or local infection. Such contaminants sometimes lead to sepsis and death. This phenomenon is further aggravated by contact of the device, such as urinary tract Foley type catheters, for example, by external mammalian tissues, such as skin or mucous membranes which themselves are carriers of potentially infective organisms.

Various proposals have been made in the past to provide protection for such devices such as catheters and various bacteriostats and bacteriocides have been applied to the surfaces of urinary catheters to prevent infection. However, none of these have been completely effective and the danger of infection and the potentially fatal problems it presents is always present, particularly in the case of indwelling catheters such as urinary tract Foley type catheters.

It has also been believed that therapeutic risk involved with the use of medical devices could be controlled, eliminated or attenuated if the device itself had antiseptic properties. Medical use and research has demonstrated that antibiotic use alone such as systemic treatment separate from local application to the device, is ineffective for long term antisepsis due to bacterial resistance and sometimes drug allergic reaction. Therefore, the use of an antiseptic agent whose anti-infective organism-effects are multi focal and wide-spectra is necessary if long term and safe antisepsis is to be imported to the device. It has become readily apparent that many agents, while not developing microorganism resistance, have a limited spectrum such as nitrofurazone and chloroxylenol, which are weakly effective against Pseudomonas and some Proteus, silver sulfadiazine, which is weakly effective against *Staphylococcus* aureus and Pseudomonas, and mandelic acid, which is weakly effective against Proteus. It has accordingly not been possible to achieve reliable long term indwelling of catheters, such as urinary catheters, capable of effective antiseptic action.

This problem has been especially prevalent in urinary retention catheters such as Foley catheters. Retention catheters connect the patient's bladder to an outside collecting system to continuously remove urine from the patient's bladder. Sources of urinary retention catheter related urinary tract infections are suspected to be bacteria progressing from the patient's meatus through the peri-urethral space into the bladder or the catheter lumen. A number of methods and devices in the prior art for attempting to prevent bacterial caused urinary tract infections are disclosed. Examples include U.S. Pat. Nos. 4,773,901; 5,098,379; 5,236,422; 5,261,896; 5,269,755 and 5,269,770. However, for many applications, these devices have not proved to be totally effective. As a result, a substantial probability of acquiring a urinary tract infection still exists when using these devices.

In addition to the contamination and infection difficulties discussed above, it is further highly desirable in many procedures to alternatively provide medicaments for other purposes. For example, it is often necessary and desirable to have catheters, tubes and other medical devices in contact with the animal or human bloodstream to deliver medication, perform hemodialysis or other therapeutic and/or diagnostic functions. These indwelling devices and their lumens often become obstructed by clotted blood rendering them non-functional. It is, therefore, important that a reliable means be provided to ensure that an effective amount of anticoagulant is administered to the problem location to prevent undesirable blood coagulation/clotting.

There are also circumstances in which formation of scar tissue is highly undesirable. This can occur during the healing of naturally occurring wounds or as a result of surgical procedures. It is beneficial and needed in both animal and human medicine to modify or "remodel" the scar formed after injury or surgery in order to effect a more near normal function. This is evident in contracture caused by burn scar, urethral stenosis following prostate surgery or injury, tracheal stenosis, in flexor tendon repair in the hand and in other procedures. However, there is a need for a vehicle in which "scar remodeller" compounds that assist in such scar modification can be reliably and continuously applied to the target tissue. Prior attempts and devices have not been completely successful in that regard.

There are many other uses for medicated polymeric devices such as implanted spermicidal devices and chemotherapeutic delivery systems.

OBJECTS OF THE INVENTION

It is accordingly an object of the present invention to provide medical apparatus having self-contained anti-coagulant properties and capable of preventing unwanted coagulation/clotting of blood in a wide variety of circumstances and applications.

It is an object of the present invention to provide a medical apparatus such as an indwelling venous catheter or an indwelling hemodialysis catheter which will prevent blood clot formation on their respective surfaces.

It is a further object of the present invention to provide medical apparatus having self-contained scar remodelling properties capable of reshaping newly formed wound scar to improve function.

It is another object of the present invention to provide medical apparatus such as a catheter having self contained antiseptic properties and capable of preventing infection against a wide variety of microorganisms.

It is yet another object of the invention to provide a catheter capable of extended periods of release of antiseptic compound, especially for preventing urinary tract infections.

It is still another object of the invention to provide a means for preventing infection in a variety of devices such as shunts, stents, catheters, cannulas, implants, tubes, bags, sheets and the like that are contacted with tissue.

It is again another object of the invention to provide a means to delivery chemotherapy by an implanted medicated polymeric apparatus.

It is still, yet again, another object of the invention to provide fertility enhancement or inhibition by the placement of a medicated polymeric device.

Other objects and advantages of the invention will become apparent to those skilled in the art from the drawings, the detailed description of detailed embodiments and the appended claims.

SUMMARY OF THE INVENTION

The present invention provides apparatus having medicinal capabilities that are dependent on the slow and continuous release of medicinal agents adapted for use over extended retention periods. The apparatus includes a structure having a reservoir located between opposed surfaces and containing a water-activated or continuously released medicinal agent. At least a portion of the structure located between the surfaces and the reservoir is formed from a material adapted to permit inward permeation of water vapor toward the reservoir and diffusion of a medicinal compound formed as a reaction product of the water-activated medicinal agent toward the surfaces of the structure.

The present invention particularly provides an apparatus used for venous medication or for hemodialysis which contains an anticoagulant agent in a reservoir which is activated by contact with water vapor or serum causing activated anticoagulant to migrate to the surface of the apparatus. This physical activation of the medicinal agent is due to the formation of a water solution of that agent from which it can partition into the silicone matrix and move out to its surfaces. Modifiers of such medicinal agent reservoirs include hydroscopic (water attracting) salts such as anhydrous calcium chloride or phosphorous pentoxide and buffering agents with which the pH of the ensuing solution may be modified, such as disodium acid phosphate, thereby modifying the ionic charge of the medicinal agent and controlling its permeatibility through the silicone membrane.

The present invention also provides a structure wherein a water-activated medicinal agent is dispersed within at least a portion of the structure. At least a portion of the structure between its opposed surfaces permits permeation of water vapor toward and into contact with the water-activated medicinal agent and diffusion of medicinal compound formed from the water-activated medicinal agent toward at least one of the opposed surfaces.

The present invention also provides for a medical apparatus containing, in at least a portion of its matrix, fertility altering medicinal agents which can be can be water vapor activated by diffusion of water vapor through the polymer and into contact with the medicinal agent.

The present invention also particularly provides an apparatus used for the delivery of chemotherapeutic agents contained in at least a portion of the polymeric structure which are either due to their chemical nature and relation to the polymeric structure, activated by water vapor diffusion through the polymeric structure.

The present invention also particularly provides a medical apparatus such as an indwelling urinary Foley catheter containing in its matrix reservoir a scar remodelling agent, such as β-aminopropionitrile fumarate, which when activated by water vapor in the presence of a buffer releases β-aminopropionitrile free base to the surface of the apparatus. The scar remodelling agent temporarily inhibits scar collagen cross-linking, allowing dynamic forces to remodel the scar to accomplish normal function.

BRIEF DESCRIPTION OF THE DRAWINGS

FIG. 2 shows a front elevational view, partly taken in section, of a catheter of the invention.

FIG. 4 is a cross-sectional view of the catheter shown in FIG. 2 at the lines and arrows IV—IV.

FIG. 5 is a cross-sectional view similar to that shown in FIG. 4 of another embodiment of the invention.

FIG. 6 is a cross-sectional view of another embodiment of a catheter similar to that depicted in FIGS. 4 and 5.

FIG. 7 is a cross-sectional view of a catheter in accordance with embodiments of the invention and including a diffusion barrier formed thereon.

FIG. 8 is a front elevational view, taken in section, of a portion of a tube having antiseptic capabilities in accordance with the invention and adapted for use in medical apparatus such as catheters, cannulas, shunts, stents, joints, implants and the like.

FIG. 9 is a perspective view of a portion of a sheet having antiseptic capabilities in accordance with the invention.

DETAILED DESCRIPTION OF THE INVENTION

Figure 1:
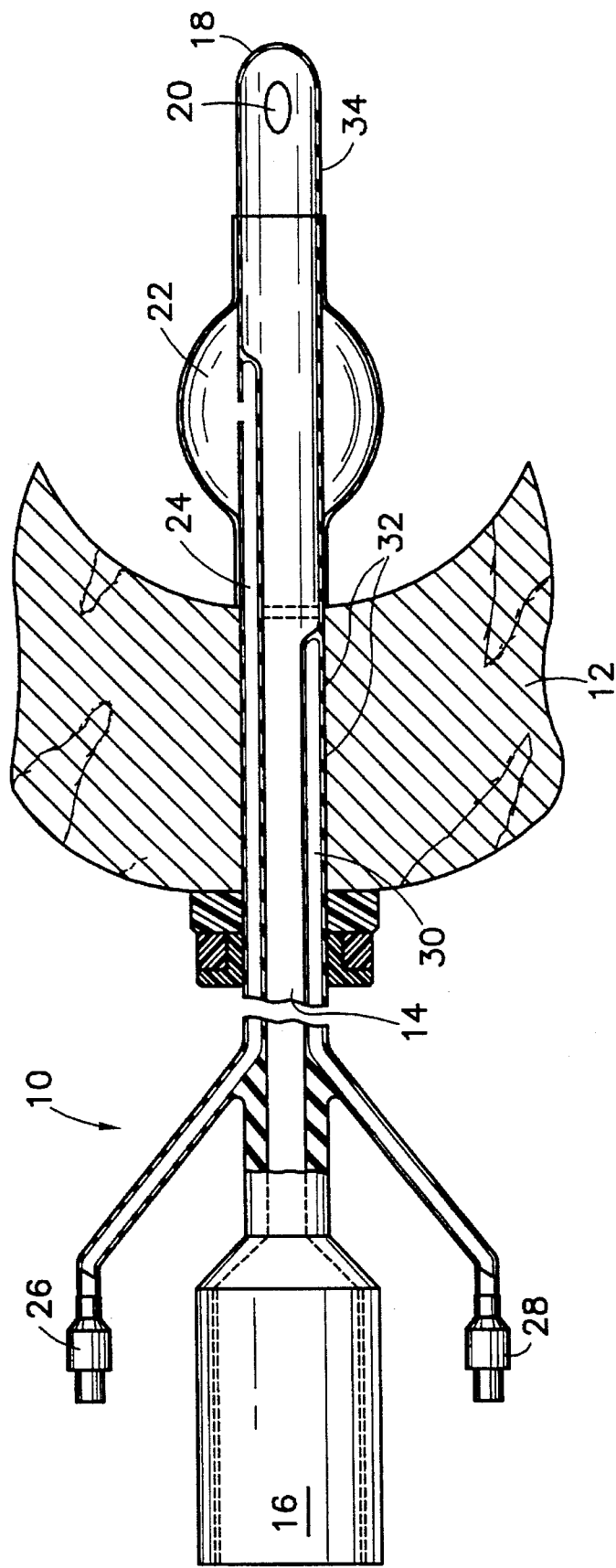
FIG. 1 shows a front elevational view, taken partly in section, of a prior art Foley-type catheter extending into a bladder.

It will be appreciated that the following description is intended to refer to the specific embodiments of the invention selected for illustration in the drawings and is not intended to define or limit the invention other than in the appended claims.

Turning now to the drawings in general, and FIG. 1 in particular, the number 10 designates a Foley-type catheter retained in a desired position relative to tissue 12. Catheter 10 includes a central lumen 14 which terminates at its proximal end in a coupling 16 and a curved tip 18 on its distal end. Tip 18 includes hole 20 for ingress of urine. Urine entering hole 20 passes along central tube 14 and outwardly of catheter 10 by way of coupling 16. The distal end also includes an inflatable balloon 22 which assists in retaining catheter 10 in position. Balloon 22 is inflated and deflated by causing inflation fluid to flow through inflation passageway 24 which connects to inflation portal 26. A medicament portal 28 connects to the proximal end of catheter 10 and is contiguous with medicament passageway 30 in catheter 10. A plurality of medicament holes 32 extend through outer surface 34 of catheter 10 and into contact with the surrounding tissue 12. Medicaments, lubricants and the like are applied to the surrounding tissue by introduction into medicament portal 28, through medicament passageway 30 and outwardly through medicament holes 32.

Although catheters of the type shown in FIG. 1, including their means for applying medicament directly to nearby tissue, are improved over prior catheters, they still retain several disadvantages such as the need for complicated and cumbersome structure. Such structure includes medicament portal 28, medicament passageway 30 and medicament holes 32, for example. From an operational standpoint, it is also necessary to repeatedly or continuously supply medicament to the affected area during the entire retention time of the catheter 10 within tissue 12. This requires constant monitoring and increased attention by attending staff. There is also a possible problem associated with inadequate application of medicament in the event that one or more of the medicament holes become plugged or there is a "short circuit." These and other problems have now been solved by the invention as described below and illustrated in the drawings.

FIG. 2 depicts one embodiment of a catheter 36 of the invention. Catheter 36 includes a tubular member 38 which connects on its proximal end to a coupling 16 and terminates at its distal end in a closed tip 18. Closed tip 18 contains hole 20 which permits ingress of urine into central lumen 14 for passage outwardly via coupling 16. Tubular member 38 has an outer surface 34 which contacts surrounding tissue and an inner surface 40 which forms central lumen 14. Catheter 36 also includes an inflation portal 26 connected to inflation passageway 24. Inflation passageway 24 connects to balloon 22 in the usual manner. However, in a sharp departure from other devices, catheter 36 is provided with a closed reservoir 42 which contains a water-activated medicinal agent. Reservoir 42 may be sized to fit the particular need, although a volume of 2000 mm$^3$ for an 18 French size Foley catheter is especially preferred.

The water-activated medicinal agent is inactive in reservoir 42 prior to use and is "activated" only upon contact with water or water vapor. In one embodiment, and upon contact, water vapor and water-activated medicinal agent "chemically" react and form reaction products, as an active molecule, which have medicinal capabilities, hereinafter referred to as "medicinal compounds." In other embodiments, water-activated medicinal agent is "physically" activated upon contact with water vapor, wherein dry, stable water-activated medicinal agent (and a buffer) is converted to a "free base" under the influence of the buffer and the free base migrates to the apparatus surface.

Another embodiment of the invention includes the dispersion of the water-activated medicinal agent within at least a portion of the catheter 36, or other device, in place of closed reservoir 42. Typically, the water-activated medicinal agent is evenly dispersed through the matrix of the material forming catheter 36 in crystalline form. Dispersion of the water-activated medicinal agent into the matrix is performed in accordance with a number of methods such as by directly mixing the water-activated medicinal agent with the matrix compound prior to curing.

The water-activated medicinal agents of the invention include water-activated antiseptic agents, water-activated anticoagulants and water-activated scar remodellers.

The preferred water-activated antiseptic agent is a halophor. Preferred halophors o include iodophors, bromophors and chlorophors. A particularly preferred iodophor is povidone iodine. Preferred bromophors are bromo-chloro-hydantoin and N-bromosuccinimide. The preferred chlorophors include oxychlorosene, trichloroisocyanuric acid and N-chloro-succinimide. The chlorophors also include N-chloro substituted amines, amides and other imides. Hypochlorite solutions and chlorinated lime also constitute chlorophors that may be used in the invention. When the iodophor povidone iodine is employed in reservoir 42, reaction with water vapor produces iodine and/or hypoiodous acid, both of which have antiseptic capabilities and are antiseptic compounds. Similarly, trichloroisocyanuric acid produces hypochlorous acid and/or chlorine as antiseptic compounds upon reaction with water vapor.

The halophors may be supplied to reservoir 42 in varying concentrations, preferably at concentrations of about 10–40%, most preferably about 20%, for a trichloroisocyanuric acid halophor and about 20–60%, most preferably about 30%, for an N-chloro-succinimide halophor.

The mechanism involved in generating antiseptic compounds from water-activated antiseptic agents is described below as it is believed to occur, although it should be understood that other mechanisms may be solely or partially responsible for the generation of antiseptic compounds from water-activated antiseptic agents. The release of chlorine ($Cl_2$) or hypochlorous acid (HOCl) from trichloroisocyanuric acid dispersed in silicone rubber matrices depends on chemical water activation. This complex chemical reaction, during which active chlorine is released, normally does not proceed in the absence of water. Only upon entry of water vapor into the matrix does the reaction begin. Water vapor ($H_2O$), chlorine ($Cl_2$) and hypochlorous acid penetrate silicone rubber while entrapped trichloroisocyanuric acid as well as cyanuric acid (its final breakdown product) do not penetrate through the silicone matrix, such as the wall of a Foley urinary catheter.

The catheter is stored in a sealed package containing a desiccant subsequent to curing which maintains the humidity around the catheter below 5% and no $H_2O$ activation occurs while the catheter is sealed. Upon insertion of the catheter into tissue, or possibly insertion after preconditioning the catheter in a sterile solution of saline, water vapor will diffuse through the walls of the catheter and chemically react with trichloroisocyanuric acid which is present within the silicon matrix as individually dispersed crystals or in a specified intramural reservoir. This reaction leads to hydrolytic cleavage of the molecule under release of hypochlorous acid as shown in Reaction 1:

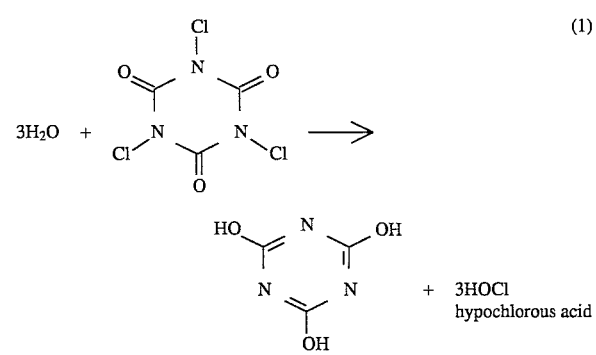

Hypochlorous acid (HOCl) can then have a number of different fates:

1. It may diffuse out of the catheter and appear on its outer or inner luminal surfaces as an antiseptic/disinfectant agent.

2. It may dismutate, that is, several molecules of hypochlorous acid react with each other to form molecules with a higher oxidation state that is chloric acid or $HClO_3$ and molecules of a lower oxidation state than hypochlorous acid, namely hydrochloric acid or HCL as shown in Reaction 2:

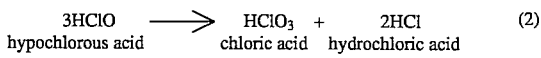

$$\underset{\text{hypochlorous acid}}{3HClO} \longrightarrow \underset{\text{chloric acid}}{HClO_3} + \underset{\text{hydrochloric acid}}{2HCl} \quad (2)$$

3. The latter hydrochloric acid (HCl) can then react with more hypochlorous acid (HOCl) to form chlorine and water as shown in Reaction 3:

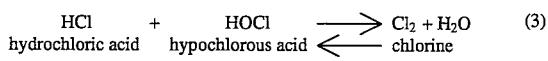

$$\underset{\text{hydrochloric acid}}{HCl} + \underset{\text{hypochlorous acid}}{HOCl} \underset{\longleftarrow}{\longrightarrow} \underset{\text{chlorine}}{Cl_2 + H_2O} \quad (3)$$

4. The chlorine itself can diffuse out of the silicone rubber material and reach the outer and inner surfaces of the catheter. Upon reaching an actual liquid water phase (mucous membranes on the outside or urine on the inside of the catheter), it will react in the opposite direction of its generation and produce HCl and HOCl as shown in Reaction 3.

The overall outcome of these reactions and diffusion phenomena is that only those agents which are diffusible in silicone rubber matrices appear on the outside, while other materials, potentially toxic to the organism, stay inside the matrix and are permanently entrapped. The former agents include hypochlorous acid and chlorine. The latter includes all other agents formed or originally present, that is trichloroisocyanuric acid, cyanuric and chloric acid.

Figure 3:
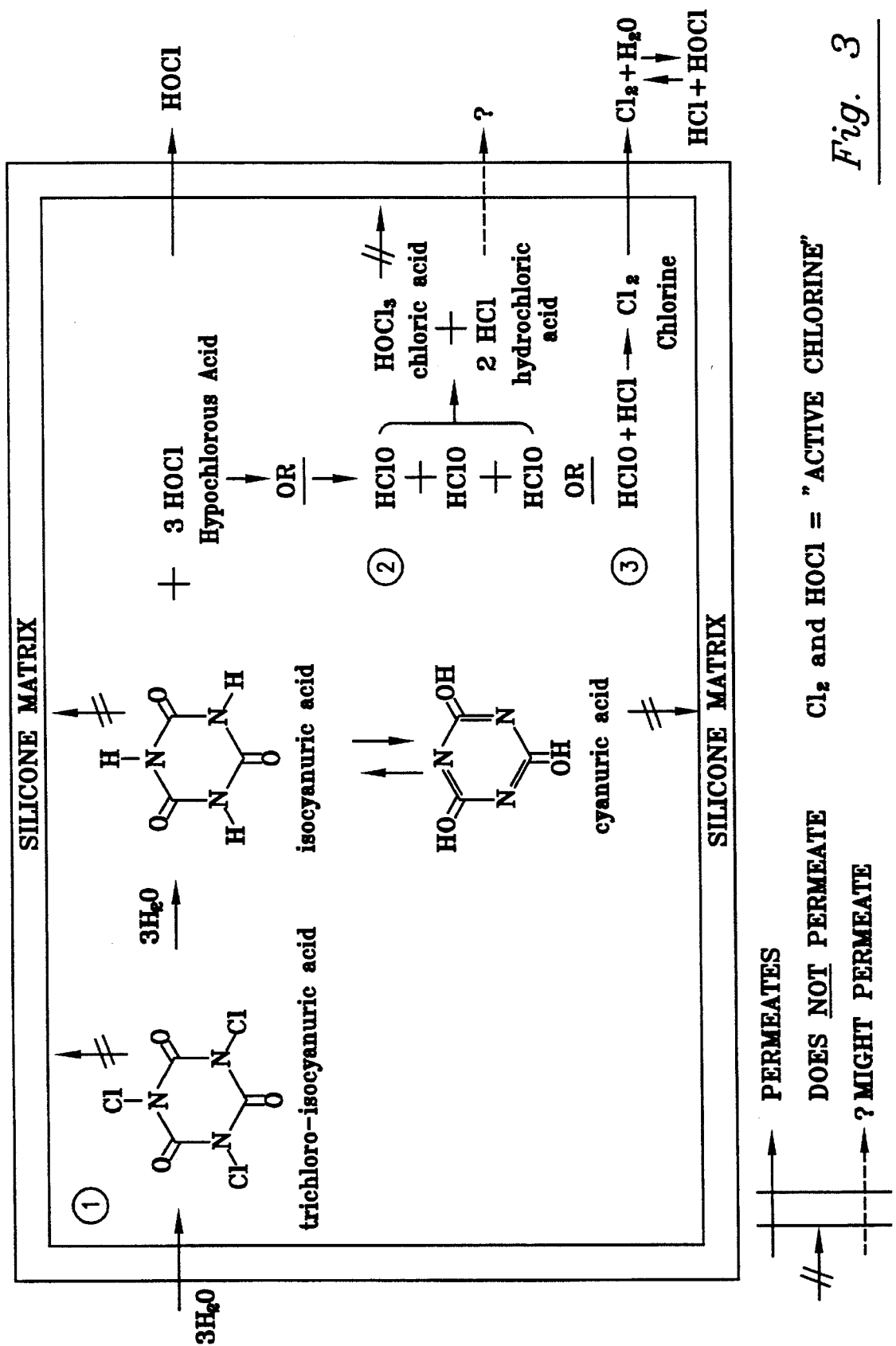
FIG. 3 is a schematic of selected chemical reactions that occur in accordance with aspects of the invention within a silicon matrix.

Along this same or similar mechanisms, other halophors, such as those listed below, react and operate as described above:

Chemically Water-Activated Halophors:
Trichloroisocyanuric acid
N-Bromo succinimide
N-Chloro succinimide
Calcium hypochlorite
Sodium Hypochlorite
Potassium dichloroisocyanurate
Oxychlorosene
Povidone-Iodine
Methenamine tetraiodine
Bromo-chloro-hydantoin FIG. 3 schematically shows reaction and penetration as described. Other compounds, such as those listed below, either permeate continuously due to their relatively high vapor pressure which allows them to enter the silicone matrix from the solid state or do not permeate at all due to their chemical nature as charged or high molecular weight compounds.

While nonpenetratable medicinals are not deliverable in these devices and are therefore not useful in this application, continuously released agents which pass from the solid state into silicone matrices are somewhat useful if their delivery to the outside can be controlled by intervening polymeric barriers, or if the device is covered with an impermeable outer mantle which can be removed before inserting or implantation. Since such devices are complex and not easily storable over extended periods of time, they are not preferred at this time. Such agents include the following compounds.

Continuously Released Halophors and Halogenated Phenols/Alcohols:
Bornyl-chloride
Cloflucarban
Fluorosalan
Iodine
Iodine monochloride
Iodine trichloride
Iodoform
Thymol iodide
Triclosan
Chloroxylenol
Dichlorobenzylalcohol
2,4,6-tribromocresol
Hexachlorophene
Fentichlor
Chlorophene Nonpenetrating Agents Carrying Halogen:
Bismuth iodo-subgallate
Calcium iodate
Iodic acid
Silver bromide
Mercurous chloride
Mercurous iodide
Potassium tetraiodomercurate
Chlorhexidine
Cetalkonium chloride
Amantanium bromide The preferred water-activated anticoagulant agents include:
Accnocouranol
Anisindione
Bromindione
Clotindione
Coumetarol
Cyclocumarol
Dicumarol
Diphenadiene
Ethyl Biscoumacetate
Ethylidene Dicoumarol
Fluindione
Oxazidione
Phenindione
Phenprocoumon
Warfarin Migration of water vapor toward and into contact with the anticoagulant causes activation of the anticoagulant by dissolution of the latter into an entrapped liquid water phase and permits migration of the anticoagulant to the surface of the apparatus. The following anticoagulants have been found not to be suitable because of their high molecular weights or charged nature, both of which lead to impenetrability of the silicone membrane. These anticoagulants include:
Anerod
Dextran sulfate sodium
Heparin
Hifudin
Lyapolate sodium
Pentosan polysulfate
Phosvitin The preferred water-activatable scar remodeller agent is β-aminopropionitrile fumarate (βAPN-F). βAPN-F, in the presence of a buffer such as $Na_2HPO_4$, hydrolyses to result in a portion of the total βAPN-F to be converted to β-aminopropionitrile (βAPN) free base, which is capable of migration through the silicone membrane to the surface of the device. The presence of βAPN inhibits collagen cross-linking which then allows scar remodeling by functional forces or by the shape of the device itself.

At least a portion of tubular member 38 located between outer surface 34 and reservoir 42 as shown in the drawings is constructed from a material which permits diffusion of water vapor from surrounding tissue inwardly toward reservoir 42 and medicinal moities produced from the water-activated medicinal agent but not their carrier molecules, such as polyvinyl pyrrolidone in the case of povidone iodine and cyanuric acid in the case of trichloroisocyanuric acid outwardly toward outer surface 34 and the surrounding tissue. In a preferred form, at least a portion of tubular member 38 located between inner surface 40 and reservoir 42 is constructed from the material to permit diffusion of medicinal compounds produced from the water-activated medicinal agent toward inner surface 40 and lumen 14. In its most preferred form, tubular member 38 is constructed entirely from the same material. An especially preferred material is elastomeric silicones such as silicone rubber. Other materials such as fluorohydrocarbons may be employed. It is especially preferred that polymeric materials selected for tubular member 38 be vulcanized polymeric materials.

In the embodiments wherein the water-activated medicinal agent is dispersed within the silicone matrix, it is preferred to employ vulcanizing silicone rubbers such as 3140RTV, manufactured by Dow-Corning or silicone rubber such as 1-2577 transparent silicone rubber manufactured by Dow-Corning, although other silicone matrix materials may be used. Dispersion of various materials into silicone matrices is well known and not discussed in detail. Water-activated medicinal agents of the invention may be dispersed within silicone matrices in a like manner.

FIG. 4 shows a cross section of the catheter shown in FIG. 2 wherein tubular member 38 contains inflation passageway 24 and reservoir 42. Reservoir 42 is located just below, but adjacent to outer surface 34 of tubular member 38.

FIG. 5 shows another embodiment of tubular member 38 of catheter 36 wherein reservoir 42 is located at a position closer to lumen 14, at a distance further removed from outer surface 34.

FIG. 6 shows still another embodiment of catheter 36 wherein lumen 14 is not centrally located along the center axis of catheter 36 and reservoir 42 is located still further away from outer surface 34. Arrows "A" represent a diffusion path for water vapor to migrate inwardly toward reservoir 42. Arrows "B" represent a diffusion path for medicinal compound to migrate inwardly and outwardly from reservoir 42.

Variations in the structure of catheter 36 as shown in FIGS. 4–6, permit variations in the medicinal activity of the medicinal compound. For example, the embodiment shown in FIG. 4 permits comparatively rapid diffusion of medicinal compound outwardly of catheter 36 relative to the diffusion rate of medicinal compound in the embodiment shown in FIGS. 5 and 6. Structural alterations such as those depicted in FIGS. 4–6 can be employed to meet a variety of conditions such as the desired retention time of catheter 36, the type of medicinal compound, the concentration of the medicinal compound, the type of microorganisms likely to be encountered, the type of surrounding tissue and the like.

An alternative structure is shown in FIG. 7 wherein a diffusion barrier 44 is concentrically positioned outwardly of tubular member 38 on outer surface 34 and a diffusion barrier 45 is inwardly positioned on inner surface 40 along lumen 14. The diffusion barrier can be selected from a wide variety of materials, so long as they permit diffusion of water vapor and the medicinal compounds, to further control the diffusion rate of medicinal agents outwardly from catheter 36. Especially preferred among the materials for the diffusion barrier are fluorinated polymeric hydrocarbons. Those materials provide the added advantage of low coefficients of friction which assists in insertion and movement of the catheter against and along sensitive surrounding tissues.

In use, catheter 36 is applied to the appropriate passageway, such as the urinary tract, a blood vessel or the like in the usual manner for the particular task. However, the amount, type and concentration of the water-activated medicinal agent in reservoir 42 or as dispersed in the matrix forming at least a portion of the device is pre-determined and pre-contained prior to insertion, thereby avoiding a wide variety of the problems of prior art devices. The water-activatable medicinal agent contained within reservoir 42 or the matrix is inactive prior to insertion and is only activated upon diffusion of water vapor through tubular member 38 and into contact with the water-activated medicinal agent in. reservoir 42 or in the matrix. Water from the surrounding tissues diffuses as water vapor through tubular member 38 in the manner indicated by arrows "A" in FIG. 6 and into reservoir 42 or the matrix.

The chemical or physical interaction between the water vapor and water-activated medicinal agent proceeds within reservoir 42 or the matrix by virtue of the diffusion that occurs over the course of time, depending on factors such as the particular water-activated medicinal agent, its concentration, the distance between reservoir 42 and outer surface 34 or lumen 14, the presence or absence of a diffusion barrier, the amount of water vapor supplied from the surrounding tissues, the water permeability of the material selected for tubular member 38 and the like. Medicinal compound then diffuses inwardly and/or outwardly as shown by arrows "B" in FIG. 6 toward outer surface 34 and lumen 14. By knowing and pre-selecting combinations of these variables, catheter 36 reliably applies medicinal compounds to the affected tissues or into lumen 14 in a manner that reliably applies medicaments to the tissues and provides for increased retention times beyond those contemplated in the art.

FIG. 8 shows a portion of a tube 46 that may be used as or in conjunction with a variety of medical devices. Such devices include catheters, shunts, stents, joints, implants, bags, cannulas and the like. Tube 46 includes a pair of reservoirs 42 located opposite one another and between outer surface 34 and inner surface 40. Each reservoir 42 contains water activatable antiseptic agent in the same manner as shown in FIGS. 2 and 4–6. Tube 46 may be flattened into a sheet or plate if desired by performing a longitudinal cut. Alternatively, a sheet or plate 50 may be directly formed, such as shown in FIG. 9, the thickness of which may be varied as needed to suit the task. The sheet or plate has a reservoir 42 and may have varying degrees of stiffness as desired. Tube 46 and sheet 50 may also have diffusion barriers applied to one or both of their surfaces as desired.

Although this invention has been described in connection with specific forms thereof, it will be appreciated that a wide variety of equivalents may be substituted for the specific elements shown and described herein without departing from the spirit and scope of this invention as described in appended claims.

For example, catheters of the invention may have a wide variety of structures, materials and shapes, all known in the art. Also, the catheters of the invention are not limited to use as urinary catheters, but may be employed in a wide variety of uses in a wide variety of mammals and in passageways wherever antiseptic/antibacterail/antimicrobial/anticoagulant or scar remodelling capabilities are required. The number of reservoirs 42 may be adjusted as desired. For example, multiple reservoirs 42 may be arranged in an end-to-end configuration, multiple reservoirs may be provided in a selected cross-section, an entire cross-section may be one reservoir, in which case the water-activated agent may be finely divided and interspersed throughout tubular member 38 having been introduced by coextrusion, and the like. Similarly, the shape and orientation of reservoirs 42 may be selected as desired.

The construction of tubular member 38 may be selected from a variety of configurations. For example, inner surface 40 and outer surface 34 need not be concentric relative to teach other and need not be similarly shaped. Shapes of all types, including but not limited to circular, square, oval, rectangular, triangular and the like are all contemplated.

Tubular member 38 may also be constructed of a multiplicity of layers to perform various tasks as desired. For example, multiple layers having different strengths, fluid resistivities, and the like may be employed, so long as the water vapor and medicinal compound diffusion characteristics adjacent reservoir 42 are retained. Moreover, it is possible to use any number of methods for forming tubular member 38 known in the art. Particularly preferred methods include extrusion and coextrusion methods known in the art. Coextrusion such as that disclosed in U.S. Pat. No. 4,533,510 is one example.

What is claimed is:

1. Water vapor-activatible apparatus comprising:

a base member at least partially formed from a water vapor selectively permeable material and a water vapor-activatible medicinal agent which, prior to activation, does not significantly diffuse from said base member, said medicinal agent being positioned within said selectively permeable material along at least a portion of said base member;

wherein said said selectively permeable material when introduced into the human body and exposed to water vapor therein, diffuses water vapor toward and into contact with said water vapor-activatible medicinal agent and after activation by water vapor diffuses reaction product formed from said water vapor-activatible medicinal agent outwardly from said base member for treatment of an adjacent area in the patient's body.

2. The apparatus defined in claim 1 wherein said sheet is extruded.

3. The apparatus defined in claim 1 wherein said water vapor-activatible medicinal agent is a water vapor-activatible antiseptic agent.

4. The apparatus defined in claim 1 wherein said water vapor-activatible medicinal agent is in crystalline form.

5. The apparatus defined in claim 1, wherein said medicinal agent is an anticoagulant agent.

6. The apparatus defined in claim 1, wherein said medicinal agent is a scar remodeler agent.

7. The apparatus defined in claim 1, wherein said medicinal agent is a chemotherapeutic agent.

8. The apparatus defined in claim 1, wherein said medicinal agent is a fertility altering agent.

9. The apparatus defined in claim 1, wherein said medicinal agent is a β-amino propionitrile which is responsive to reaction with diffused water vapor to make a reaction product that is capable of diffusing outwardly through said selectively permeable material to accomplish said treatment.

10. A water vapor-activatible medicinal tube for venous medication or for hemodialysis comprising:

an elongated conduit having an inner surface and an outer surface, said inner surface defining a passageway extending along at least a portion of said tube, and a water vapor-activatible medicinal agent dispersed within said conduit along at least a portion of said tube;

wherein at least a portion of said conduit is formed from a selectively permeable material which diffuses water vapor toward and into contact with said water vapor-activatible medicinal agent and diffuses reaction product formed from said water vapor-activatible medicinal agent toward said inner and/or outer surfaces.

11. The tube defined in claim 10 adapted for use in a medical device selected from the group consisting of shunts, stents, cannulas, implants, joints, catheters irrigating tubes and drainage tubes.

12. The tube defined in claim 10 wherein said water-activated medicinal agent is selected from the group consisting of water-activated antiseptic agents, water-activated anticoagulant agents, scar remodeller agents, chemotherapeutic agents and fertility altering agents.

13. A catheter comprising:

an elongated conduit having an inner surface and an outer surface, said inner surface defining a lumen extending along at least a portion of said catheter, and a water vapor-activatible scar-remodelling medicinal agent in the form of a β-amino propionitrile compound which when activated by water vapor releases scar-remodelling β-amino propionitrile within said conduit along at least a portion of said catheter;

wherein at least a portion of said conduit is formed from a selectively permeable material which diffuses water vapor toward and into contact with said water vapor-activatible β-amino propionitrile medicinal agent and diffuses reaction product formed from said water vapor-activatible medicinal agent toward said inner and/or outer surfaces and through said lumen for treatment of said human body.

14. The catheter defined in claim 13, wherein said water-activated medicinal agent is selected from the group consisting of antiseptic agents, anticoagulant agents, scar remodeller agents, chemotherapeutic agents and fertility altering agents.

15. The catheter defined in claim 13, wherein said material is silicone rubber.

16. The catheter defined in claim 13, wherein said material is a fluorinated polymeric hydrocarbon.

17. The catheter defined in claim 13, wherein said catheter is a Foley catheter.

18. A catheter for insertion into a passageway in a mammal comprising:

an elongated tubular member having an inner wall and an outer wall, at least a portion of said tubular member being formed from a selectively permeable material which diffuses water vapor through said outer wall, and a water vapor-activatible medicinal agent which is essentially not diffusable through said tubular member and is capable of being stored therein, dispersed inwardly of said outer wall which medicinal agent reacts with water vapor from said mammal passageway and forms a diffusable medicinal compound as a reaction product which diffuses through said outer wall for treatment of said mammal.

19. The catheter defined in claim 18, wherein said is a uninary catheter.

20. Water vapor-activatible medicated apparatus comprising:

a base member having opposed surfaces; and storage means located within said base member, said storage means containing a water vapor-activatible medicinal agent which does not essentially react with said base member, wherein at least a portion of said base member is constructed from a selectively permeable material which diffuses water vapor toward and into said storage means for reaction with said medicinal agent to make a reaction product that is capable of permeating out of said storage means, and diffuses medicinal agent reaction product formed from said water vapor-activatable medicinal agent out of said base member.

* * * * *